(12) United States Patent
Chen et al.

(10) Patent No.: US 12,357,376 B2
(45) Date of Patent: Jul. 15, 2025

(54) RESPIRATORY COMPENSATED ROBOT FOR LIVER CANCER TREATMENT

(71) Applicant: BOARD OF TRUSTEES OF THE UNIVERSITY OF ARKANSAS, Fayetteville, AR (US)

(72) Inventors: Yue Chen, Fayetteville, AR (US); Mishek Musa, Fayetteville, AR (US)

(73) Assignee: Board Of Trustees Of The University Of Arkansas, Little Rock, AR (US)

(*) Notice: Subject to any disclaimer, the term of this patent is extended or adjusted under 35 U.S.C. 154(b) by 911 days.

(21) Appl. No.: 17/525,461

(22) Filed: Nov. 12, 2021

(65) Prior Publication Data

US 2022/0142702 A1 May 12, 2022

Related U.S. Application Data

(60) Provisional application No. 63/113,050, filed on Nov. 12, 2020.

(51) Int. Cl.
*A61B 18/14* (2006.01)
*A61B 17/00* (2006.01)
*A61B 18/00* (2006.01)
*A61B 34/30* (2016.01)

(52) U.S. Cl.
CPC ............... *A61B 18/1477* (2013.01); *A61B 2017/00398* (2013.01); *A61B 2017/00557* (2013.01); *A61B 2018/00184* (2013.01); *A61B 2018/00529* (2013.01); *A61B 2018/00577* (2013.01); *A61B 34/30* (2016.02)

(58) Field of Classification Search
CPC ............ A61B 18/1477; A61B 34/30; A61B 2017/00398; A61B 2017/00557; A61B 2018/00529; A61B 34/25; A61B 2017/3407; A61B 2017/3409; A61B 2034/302; A61B 2090/3762
See application file for complete search history.

(56) References Cited

U.S. PATENT DOCUMENTS 11,751,956 B2 * 9/2023 Arnold .................. A61M 5/46
606/130

* cited by examiner

*Primary Examiner* — Julian W Woo
(74) *Attorney, Agent, or Firm* — Keith A. Vogt; Keith A. Vogt, Ltd.

(57) ABSTRACT

A robotic platform system having a lower stage with a motorized cartesian carriage, an upper stage, and a needle insertion module that connects both stages together.

18 Claims, 18 Drawing Sheets

RESPIRATORY COMPENSATED ROBOT FOR LIVER CANCER TREATMENT

RELATED APPLICATIONS

This application claims priority to U.S. Provisional Application No. 63/113,050, filed on Nov. 12, 2020, which is incorporated herein in its entirety.

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BACKGROUND OF THE INVENTION

Primary liver cancer, also known as hepatocellular carcinoma (HCC), is the third most common cause of cancer-related death in the world with over 700,000 deaths reported annually. In the United States, an estimated 42,000 adults are diagnosed with liver cancer each year, and the number of cases is expected to continuously rise due to the increasing number of chronic liver diseases caused by alcohol, nonalcoholic fatty liver disease, hepatitis B, and hepatitis C infection. The five-year survival rate for patients is as low as 4%. As a result, there is a considerable economic loss of upwards of $1 billion per year in the United States. HCC can be treated with a variety of methods. Medical therapies, such as sorafenib, provides no reduction to the mortality rate as it only prolongs survival for a few months. Chemotherapy fails to provide effective treatment to control tumor growth, primarily due to HCC's resistance to radiation. Liver transplantation and partial surgical resection have both been shown to be effective methods of treatment, however, they both require strict criteria for candidate selection, and this prevents the majority of diagnosed patients from receiving treatment. Stereotactic radiosurgery (SRS) is a feasible approach for patients who are not eligible for liver transplantation or surgical resection; however, randomized clinical trials are still needed to justify its effectiveness. Thermal therapy, such as radiofrequency ablation (RFA), has been regarded as an effective method to control tumor growth with an acceptable morbidity rate. The main advantages of thermal therapy include 1) minimally invasive with a high safety profile, 2) capability to enable the focal tumor control, 3) favorable long-term survival rates, and 4) it can be combined with other treatment approaches. Despite the promising benefits provided by RFA, it does present some clinical limitations. Due to the limited ablation volume and heat shrink effect within the liver tissue, the ablation needle has to be accurately placed within the tumor to create the desired coagulation zone to encompass the entire target. However, manually placing the RFA needle into the tumor within the dynamically moving liver has been a long-standing challenge, even with intra-procedural image guidance. Needle targeting error is mainly caused by the respiration-induced movement of the liver, which can be as large as 5.5 cm in the superior-inferior direction. To address this issue, breath holding is typically required during the placement of the needle to mitigate the motion. However, it can be difficult for the patient to hold their breath due to compromised lung capacity and the significant pain associated with the radiofrequency ablation procedure.

BRIEF SUMMARY OF THE INVENTION

In one embodiment, the present invention provides a robotic platform that enables accurate needle deployment in the dynamic environment of the liver. The robotic platform has the following features: (1) a lightweight, compact profile that can be mounted on the patient directly; (2) provides precise ablation needle position and orientation; and (3) stepwise needle insertion that mimics the human insertion procedure.

In other embodiments, the present invention, provides a respiratory compensated robot for liver cancer treatment by providing an effective and efficient platform for the deployment of radiofrequency ablation needles. The patient mounted robot consists of a 4-DoF dual-stage cartesian platform used to control the position of a 1-DoF needle insertion module. The robot is biologically inspired as its grasp-insert-release technique of needle deployment mimics current practices used by clinicians, however with much greater accuracy. In comparison to previously developed robots for needle interventions, the present invention is capable of implementing an active motion compensation protocol that minimizes any errors caused by the respiratory-induced motion of the liver. The position of the compact and lightweight robot on the patient can easily be adjusted to their comfort levels as compared to other robots in the past that are either large in size or don't interface with the patient at all, leading to potential targeting errors.

In another embodiment, the present invention concerns a 5 degrees of freedom (DoF), patient mounted robot to perform percutaneous needle interventions for medical procedures such as the treatment of hepatocellular carcinoma.

In another embodiment, the present invention concerns a robot that includes a dual cartesian platform with a custom 3D printed active needle insertion module.

In another embodiment, the present invention concerns a robot designed to be directly mounted onto the patient's abdomen.

In another embodiment, the present invention concerns a robot deploying a step-wise needle insertion module with an active motion compensation protocol design to reduce targeting errors that may be caused by the respiratory induced motion of the patient.

In another embodiment, the present invention concerns a robot where, in free-space testing, the accuracy of the dual cartesian platform was shown to have a mean error of 0.18±0.18 mm in the x-direction, and a mean error of 0.32±0.23 mm in the y-direction.

In another embodiment, the present invention concerns a robot where, in free-space testing, the needle insertion module has an insertion accuracy of 0.64±0.38 mm along the axis of the needle, with good repeatability indicated by an average CV of 0.65%.

In another embodiment, the present invention concerns a robot where the mean positional error is around 1.14±0.30 mm, and the mean orientational error is around 0.99±0.36°.

In another embodiment, the present invention concerns a robot where the mean positional error is around 1.22±0.31 mm, and the mean orientational error is around 1.16±0.44°.

In another embodiment, the present invention concerns a robot where the mean orientational error is around 1.66±0.50°.

In another embodiment, the present invention concerns a robot having a 66.3% to 69.6% improvement in positional accuracy when an active motion compensation protocol is implemented.

In another embodiment, the present invention concerns a robotic platform system that enables accurate needle deployment in the dynamic environment of the liver comprising: (1) a lower stage with a motorized cartesian carriage, (2) an upper stage, and (3) a needle insertion module that connects both stages together.

In another embodiment, the present invention concerns a robotic platform wherein the upper and lower stages have carriages that can move in both the x and y directions.

In another embodiment, the present invention concerns a robotic platform wherein the carriages both have spherical bearings set into them that support the needle insertion module and by changing the relative location between the bearings, the orientation of the needle insertion module can be controlled about the x and y axes.

In another embodiment, the present invention concerns a robotic platform wherein the needle insertion module includes a flexible fluidic actuator adapted to insert and retract a needle.

In another embodiment, the present invention concerns a robotic platform wherein the flexible fluidic actuator includes one or more inflatable bellows adapted to move a needle linearly when the bellows are inflated.

In another embodiment, the present invention concerns a robotic platform wherein the flexible fluidic actuator includes one or more diaphragms that hold a needle stationary within the robot when inflated.

In another embodiment, the present invention concerns a robotic platform wherein, when a needle is to be inserted further into a patient, the one or more diaphragms are inflated prior to the inflation of the bellows.

In another embodiment, the present invention concerns a robotic platform wherein the upper and lower stages are identical.

In another embodiment, the present invention concerns a robotic platform further including a linear optical encoder and a linear transmissive strip, the optical encoder and linear transmissive strip adapted to provide the relative displacement of the FFA.

In another embodiment, the present invention concerns a robotic platform further including a gap between the needle and the diaphragm and bellows when the diaphragms and bellows are deflated.

In another embodiment, the present invention concerns a robotic platform wherein the gap eliminates contact between the needle and the bellows and the diaphragm when the bellows and the diaphragm are deflated.

In another embodiment, the present invention concerns a robotic platform wherein the needle does not contact the bellows and the diaphragm when the bellows and the diaphragm are deflated.

In another embodiment, the present invention concerns a method for accurate needle deployment in the dynamic environment of the liver comprising the steps of: providing a robotic platform having (1) a lower stage with a motorized cartesian carriage, (2) an upper stage, and (3) a needle insertion module that connects both stages together; the upper and lower stages have carriages that can move in both the x and y directions; the insertion module includes of a fluidic actuator adapted to insert and retract a needle; the flexible fluidic actuator includes one or more inflatable bellows adapted to move a needle linearly when the bellows are inflated and one or more diaphragms that hold a needle stationary within the robot when inflated; when a needle is to be inserted during a static phase of a liver, the one or more diaphragms are inflated to grip the needle, then the one or more bellows are inflated to insert the needle; and prior to a liver transitioning out of a static phase, the one or more inflatable diaphragms are deflated and then the one or more bellows are deflated.

In another embodiment, the present invention concerns a robotic platform wherein the needle is allowed to move freely without interference within the fluid actuator when the needle is not being inserted.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

Figure 1:
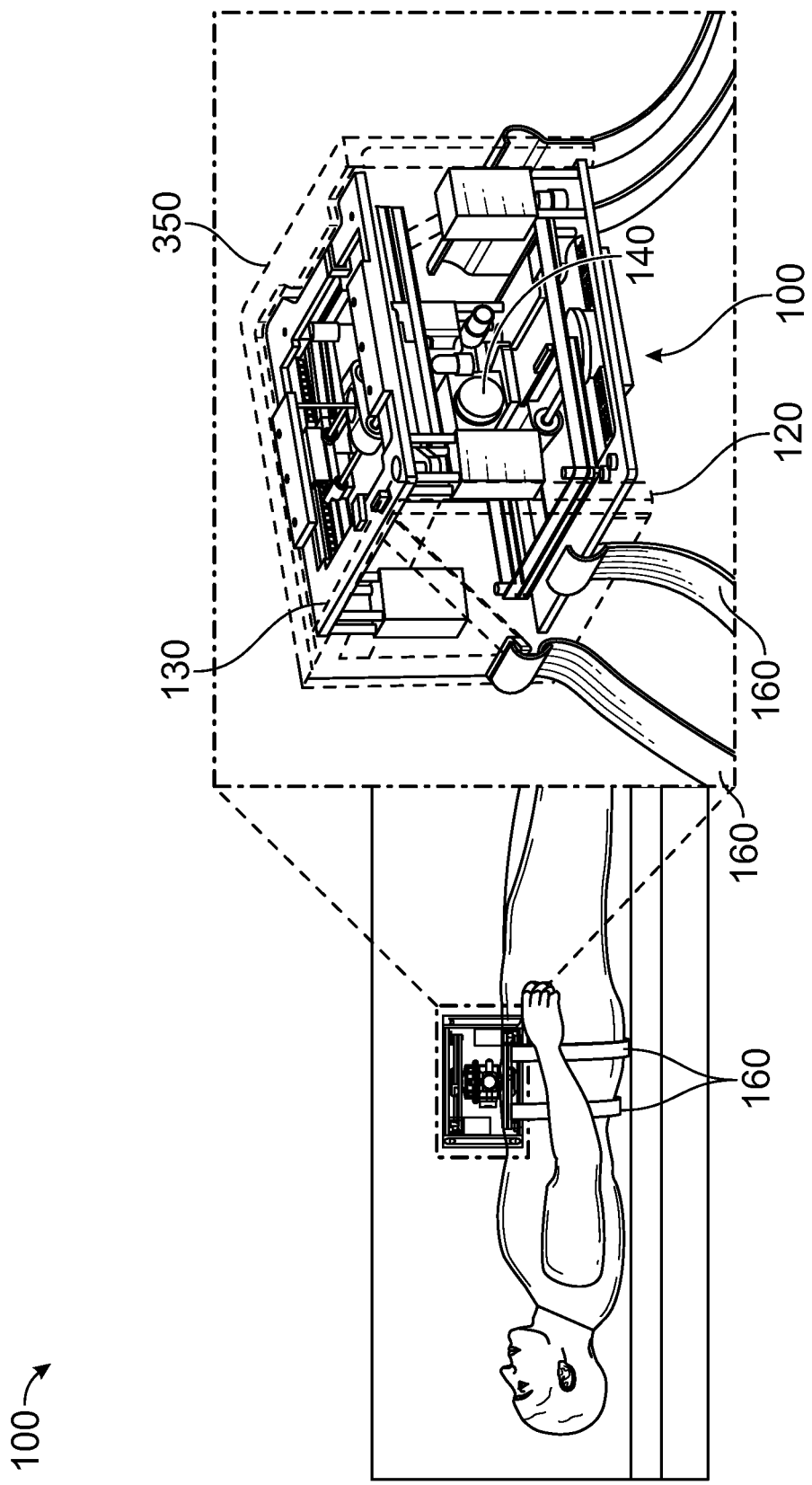
FIG. 1 illustrates an embodiment of the present invention concerning a liver ablation robot mounted on the patient within CT scanner.
Figure 2:
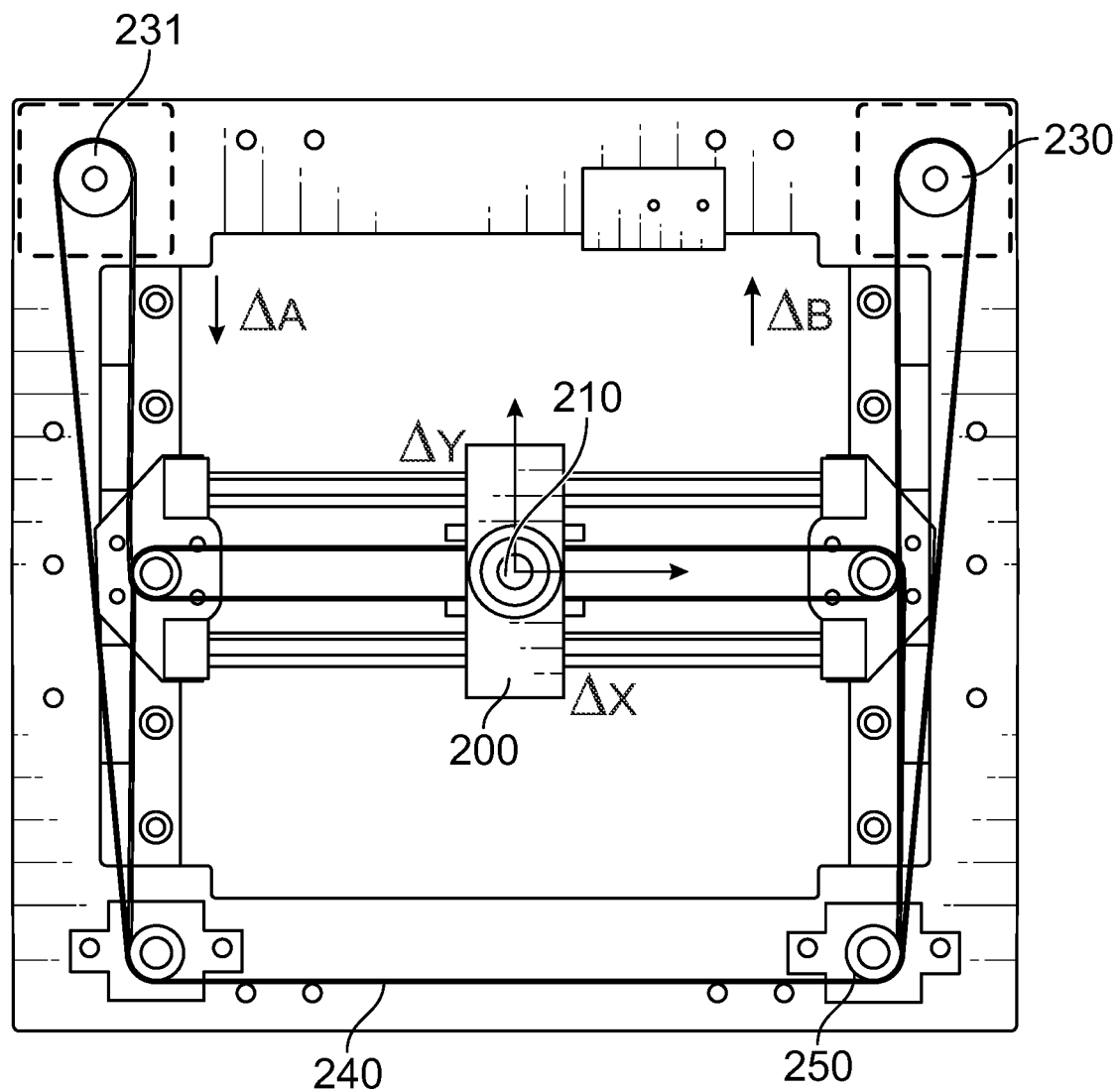
FIG. 2 illustrates a cartesian stage for use with an embodiment of the present invention.
Figure 3:
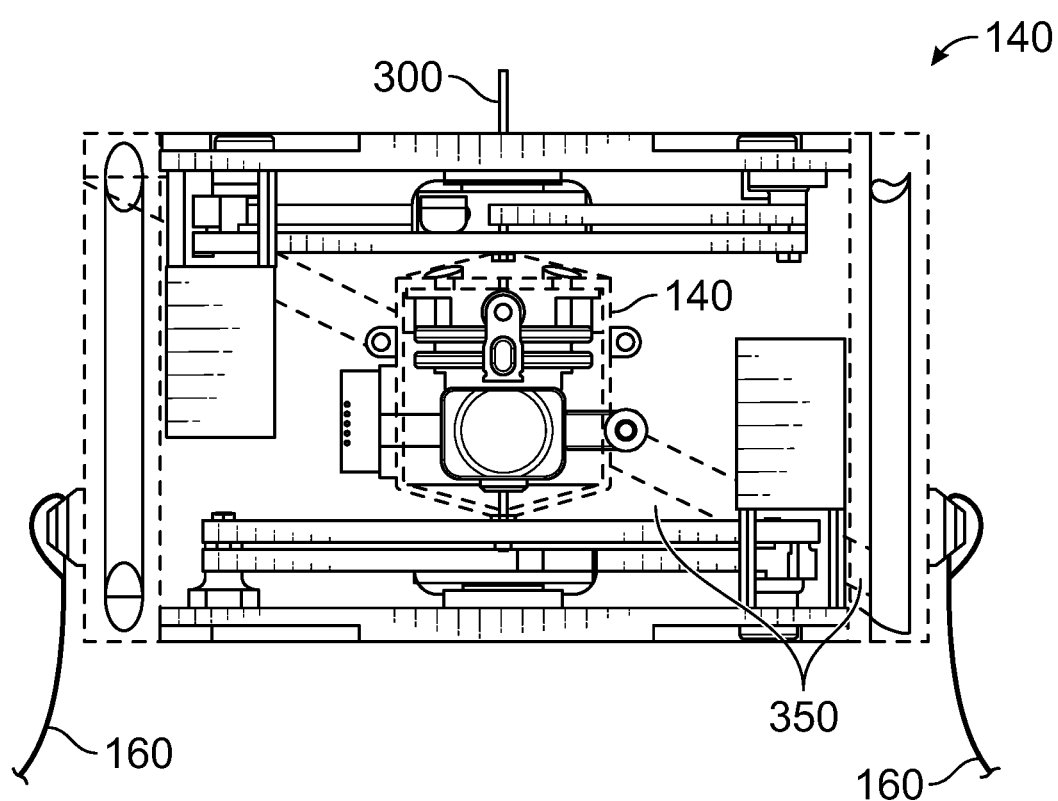
FIG. 3 illustrates the stages of the present invention connected by a Z-frame.

In one embodiment, as shown in FIG. 1, the present invention provides a robot 100 that is sized to fit within a CT scanner. The robot consists of three major subsystems: (1) a lower stage 120 with a motorized cartesian carriage, (2) an identical upper stage 130, and (3) a needle insertion module 140 that connects stages 120 and 130 together. The upper and lower stages have, as shown in FIG. 2, carriages 200 that can move in both the x and y directions (2 DoF). The carriages both have spherical bearings 210 set into them that support the needle insertion module. By changing the relative location between bearings 210, the orientation of needle 300 (as shown in FIG. 3) insertion module 140 can be controlled about the x and y axes (2 DoF). The needle insertion module can both insert and retract needle 300 through the use of a flexible fluidic actuator 310 (1 DoF) as shown in FIG. 3. Robot 100 is housed within a 3D-printed Z-frame 350 for purposes of locating the robot within the CT-scanner. As further shown in FIG. 1, Z-frame 350 includes adjustable straps 160 to attach robot 100 on the patient's abdomen according to their comfort. The overall dimensions of the robot are 216 mm×210 mm×130 mm, ensuring a compact design such that the patient can comfortably fit within the CT bore with the robot.

As further shown in FIG. 2, upper and lower motorized cartesian stages 120 and 130 include two fixed stepper motors 230 and 231 and provides a means of moving both axes independently or simultaneously. The stationary motors have the added benefit of reducing the number of moving parts, increasing the acceleration capabilities of the robot, maintaining constant hardware gravity, and allowing for a more compact design to be implemented. The carriages are driven by a series of timing belts 240 attached to the output shaft of four bipolar NEMA 11 stepper motors and the acrylic base frame using friction-reducing pulleys. Limit switches are used to set the home position of the carriages. Bearing housings 250, shaft couplers and the carriages are FDM 3D printed using the material acrylonitrile butadiene styrene (ABS). The low-level control of the cartesian stages is done on a microcontroller (ATmega 2560) with its supporting circuit. The two stages are fixed parallel to each other and held in place by support tabs attached to the fiducial registration Z-frame.

Figure 4:
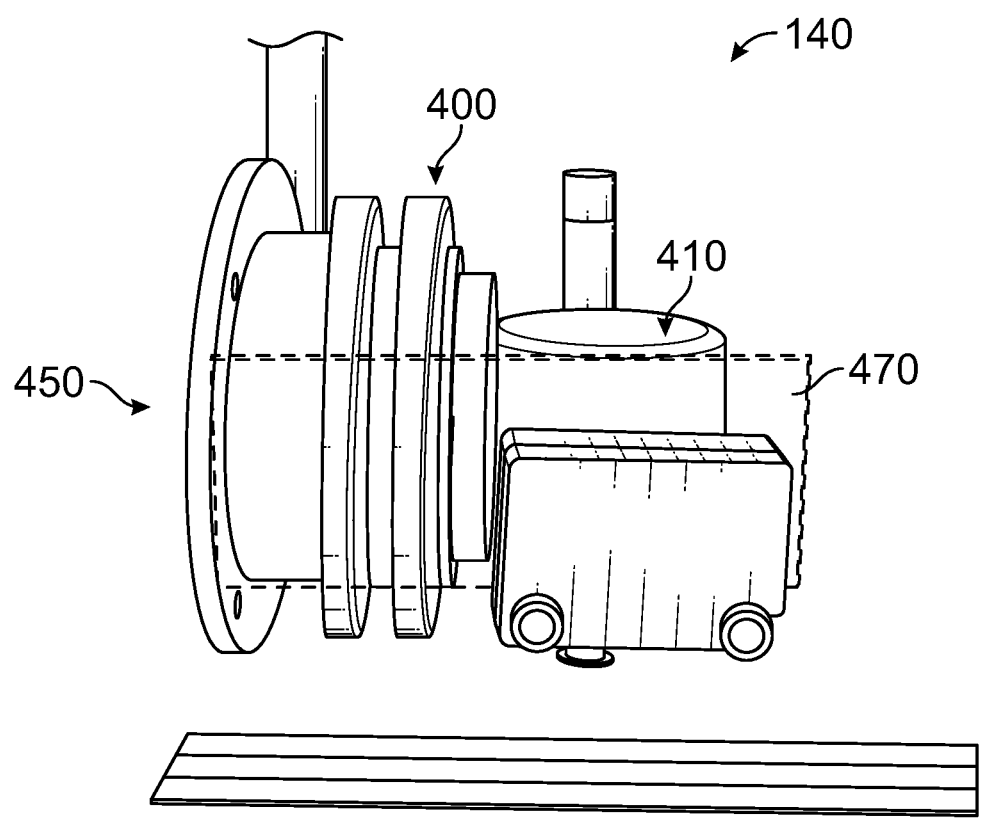
FIG. 4 illustrates a flexible fluid actuator used with an embodiment of the present invention.
Figure 5:
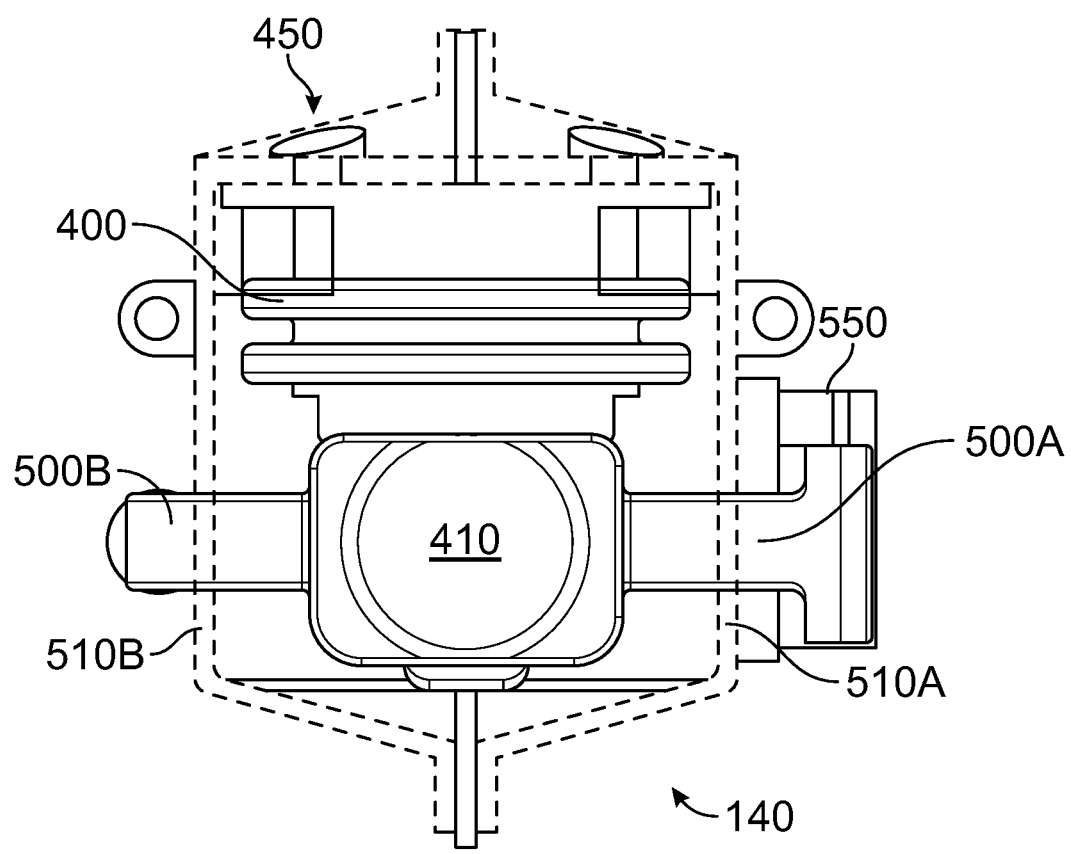
FIG. 5 illustrates the flexible fluid actuator mounted to a housing.
Figure 6:
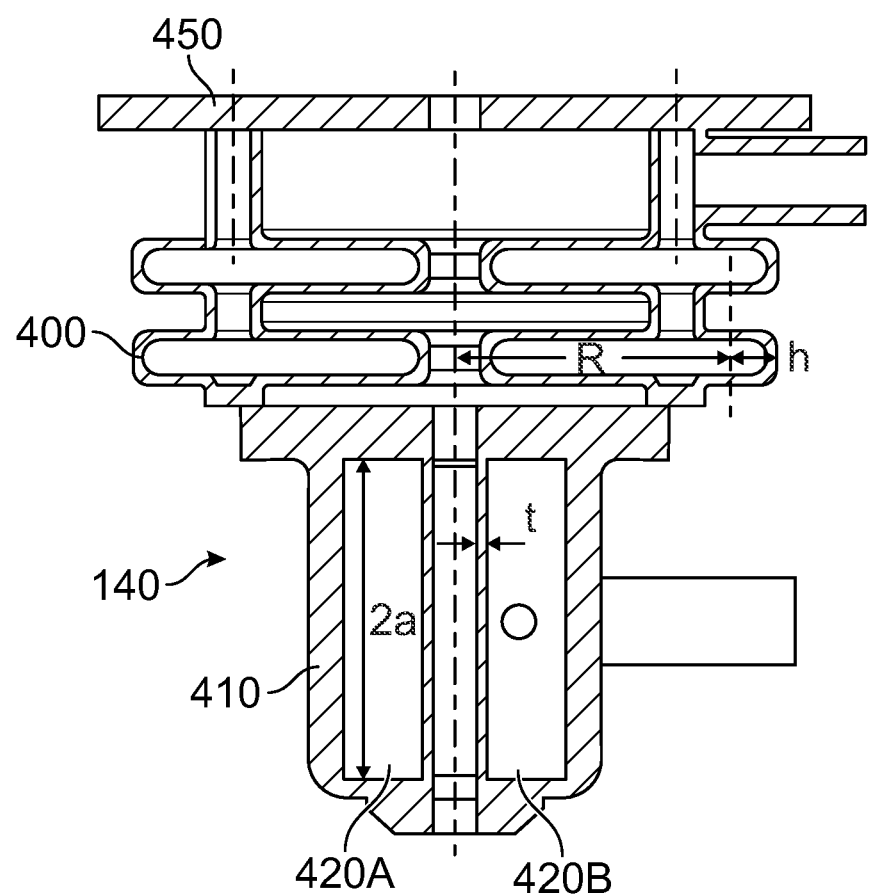
FIG. 6 is a cross-sectional view of a flexible fluid actuator along with parameters used in a force estimation analysis.

As shown in FIGS. 4-6, needle insertion module 140 consists of two components that allow for 1-DoF needle insertion: (1) linear bellow actuator 400 and (2) needle gripper 410. The mechanism is also referred to as a flexible fluidic actuator (FFA) since both components are actuated using pressurized air. The linear bellow actuator consists of a toroidal geometry such that the hollow center, which when pressurized with air, expands enabling the translation or movement of needle 300 through the central axis of the device. Under operation, needle 300 can be grasped using the gripper mechanism 410. As shown in FIG. 6, gripper 410 consists of one of more diaphragms 420A and 420B, that when inflated, expand to grasp needle 300. By grasping the needle, then inflating the bellows, needle insertion is achievable. FFA 450 may be 3D printed in the material nylon-12 using selective laser sintering (SLS). Additionally, as shown in FIG. 5, one or more safety tabs 500A and 50B may be used to restrict the linear translation of the mechanism to <2 mm. The safety tabs are important to ensure safe operation of the device to within only one full step of FFA 450 in the event of a system failure. FFA 450 is housed within an FDM 3D printed housing that consists of mechanical stop brackets 510A and 510B to both restrict the linear displacement of the FFA as well as constrain the displacement to pure translation. The safety tabs on the FFA are designed to fit into these brackets and the step-size of the mechanism can then be adjusted accordingly. Attached to the housing is a linear optical encoder 550, while a linear transmissive strip 470 (as shown in FIG. 4) is mounted to the safety tab on the FFA, so that the relative displacement between the housing and FFA could be measured to determine the insertion or retraction depth of the needle. The FFA was controlled using two proportional directional control valves with the control signal supplied via a microcontroller and amplifier circuit.

Attached to the housing is an optical encoder (US-Digital part no. EM1-1-500-N), and a linear transmissive strip (500 lines per inch) is mounted to the safety tab on the FFA. This is done so that the relative displacement between the housing and FFA could be measured to determine the insertion or retraction depth of the needle. The FFA was controlled using two proportional directional control valves (Festo MPYE-5-M5-010-B) with the control signal supplied via a microcontroller (ATmega 2560) and amplifier circuit.

Figure 7:
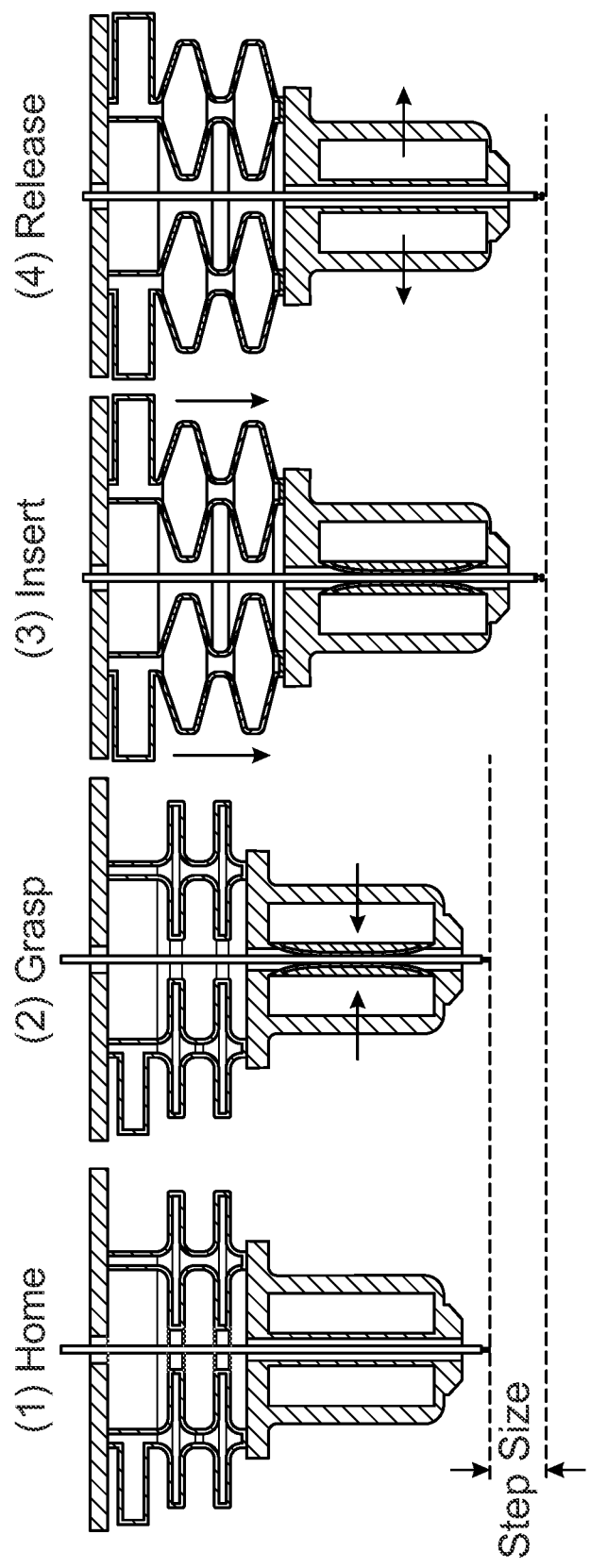
FIG. 7(a) illustrates the sequential step-like grasp-insert-release method of actuation of the needle insertion module as well as how the linear bellow will be depressurized to the home position after the release step.
FIG. 7(b) shows the static and dynamic phases of an in-vivo porcine liver.
Figure 7:
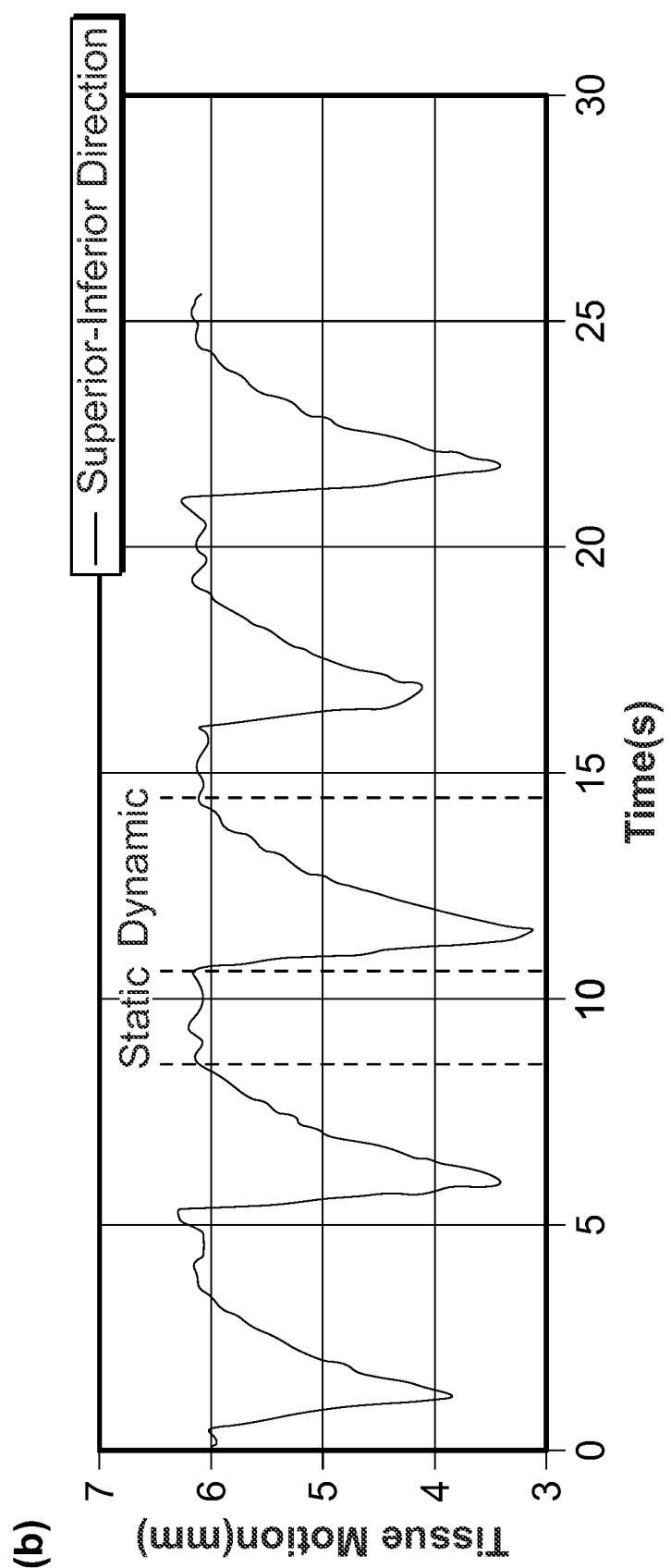
Figure 8:
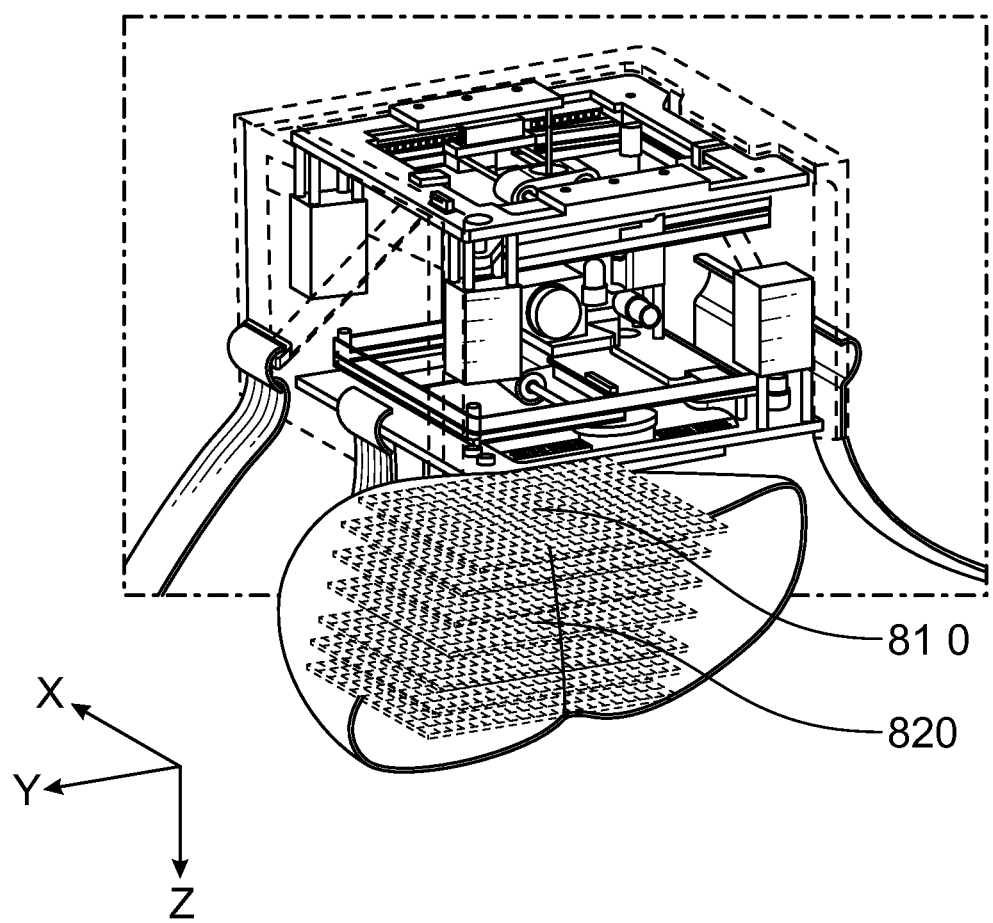
FIG. 8 provides the coordinate frame assignment of the patient mounted robot. Forward kinematics indicates that the robot workspace (blue point cloud) is able to cover 70% of the liver.

The robot is controlled using a Matlab implemented GUI that communicates to the main microcontroller via serial bus. An active motion compensation protocol is proposed for operating the patient mounted robot. As shown in FIG. 7, in this protocol, the ablation needle will be deployed towards the liver tumor during the stationary phase of the respiration cycle which is when the liver has the least motion and releases the needle when respiration induced motion is significant. Specifically, prior to the static phase of the liver, the needle is in a home position. When the liver enters a static phase, the needle is first grasped by the actuation of diaphragms 420A and 420B which occurs when the diaphragms are pressurized. The needle is then inserted a predetermined distance by the actuation of linear bellows 400. Prior to the liver entering a dynamic phase the pressure being supplied to the linear bellows and gripper is released, leaving the needle in place in a patient. As shown in FIG. 8, this process is repeated as the needle travels from the point of entry 810 to the target area 820.

Using inflatable components has several advantages. First, different size needles may be accommodated by the mechanism. Second, the components may be completely retracted away from a needle to create sufficient spacing or a gap between the FFA and the needle thereby eliminating potential unwanted movement of the needle during any movement of the liver. Thus, when the liver is in the static phase, the needle may be inserted. When the liver is in a dynamic phase, reducing or eliminating the contact between the needle and the device prevents any unwanted repositioning of the needle in the liver due to movement of the liver. In a preferred embodiment, the needle does not touch the FFA at all during periods when the needle is not being inserted.

With the CT Real-Time Position data feedback, the needle insertion module must complete a full-step insertion when the liver has negligible movement in its static phase and release the needle when the liver undergoes significant movement during its dynamic phase. The periodically moving target can be approximated to an "immobilized" point with this "move-pause" needle insertion protocol.

Several experiments were conducted in order to characterize the performance of the robot: a) free-space accuracy evaluation of the 4-DoF dual cartesian stages, b) free-space accuracy and force characterization of the active needle insert unit, c) static phantom and ex-vivo porcine targeting, d) dynamic phantom targeting, and e) dynamic ex-vivo tissue targeting.

a) Free-space accuracy evaluation of the 4-DoF dual cartesian stages revealed mean positional error in the x-direction of 0.18±0.18 mm and a mean error in the y-direction of 0.32±0.23 mm.
b) Free-space accuracy evaluation of the active needle insertion module revealed mean needle placement error of 0.64±0.38 mm. Force characterization of the active needle insertion module shows a peak frictional force between the gripper mechanism and the needle of 22.6±0.40 N indicating the force at which the needle would slip.
c) Static phantom targeting trials showed a mean positional targeting accuracy of 1.14±0.30 mm and a mean orientational targeting accuracy of 0.99±0.36°. Static ex-vivo porcine liver targeting trials showed a mean positional targeting accuracy of 1.22±0.31 mm and a mean orientational targeting accuracy of 1.16±0.44°.
d) Using the active motion compensation protocol, dynamic phantom targeting trials showed a mean positional error of 1.69±0.66 mm and a mean orientational error of 1.66±0.50°. Without the active motion compensation protocol implemented, dynamic phantom targeting trials showed a mean positional error of 5.02±2.35 mm and a mean orientational error of 4.54±1.40°.
e) Ex-vivo porcine liver targeting trials were used to represent insertion into biological tissue. Using the active motion compensation protocol, dynamic porcine liver targeting trials showed a mean positional error of 1.54±0.55 mm and a mean orientational error of 1.68±0.47°. Without the active motion compensation protocol implemented, dynamic porcine liver targeting trials showed a mean positional error of 5.07±2.44 mm and a mean orientational error of 4.06±1.45°.

Forward and Inverse Kinematics

The coordinate frames, $F_{upper}$ and $F_{lower}$, for the upper and lower stages are defined identically as being at the center of the spherical bearings in the carriages when both stages are in the homed position as seen in FIG. 8. The positions of the center of the upper and lower carriages are denoted by $O_{upper}=(x_u, y_u, z_u)$, and $O_{lower}=(x_l, y_l, z_l)$ respectively. The x and y positions of the carriages can be written in terms of the equations of motion governing the mechanism that relate motor rotation $\Delta A$ and $\Delta B$ to translation, given by $$\Delta x = \tfrac{1}{2}(\Delta A + \Delta B) \quad (1)$$

$$\Delta y = \tfrac{1}{2}(\Delta A + \Delta B) \quad (2)$$

The forward kinematics of the robot takes the joint space positions $[x_u, y_u]$, $[x_l, y_l]$ along with the desired needle insertion depth, l, and solves for the position of the tip of the needle, in addition to the needle axis vector. The positions of the center of the carriages would then be defined as $O_{upper}=(x_u, y_u, 0)$ and $O_{lower}=(x_l, y_l, -H)$, where H is the constant distance maintained between the two parallel stages of the cartesian platform. The unit vector, $\hat{N}$, defining the axis of the needle could then be given by the normalized vector of the difference between the positions of the center of the upper and lower carriages. Using this needle axis vector, for the position of the of the tip of the needle, $T_{desired}$ using the insertion depth may be solved. The equations defining $\hat{N}$ and $T_{desired}$ are $$\hat{N} = \frac{O_{lower} - O_{upper}}{\|O_{lower} - O_{upper}\|} \quad (3)$$

$$T_{desired} = O_{lower} - l\hat{N} \quad (4)$$

The robot workspace was simulated in Matlab across the achievable translations in the x- and y-directions of the cartesian stages described in Table 1.

TABLE 1

FIG. 1.
CAD model of the liver ablation robot mounted on the patient within CT scanner.
Robot Properties Based on Design and Workspace Analysis

| | |
|---|---|
| Robot Dimensions | 216 mm × 210 mm × 130 mm |
| Active DoF | 5 |
| x-y Displacement | 75 mm × 70 mm |
| Insertion Depth | Limited by Needle Length |
| Orientation about x and y axes | ±15° |
| Weight | 2.17 kg |

The markings on FIG. 8 show the workspace of the robot and it is overlaid with an average adult human liver. Comparing the volume of the workspace to that of an average adult human liver, the robot can reach 70% of the volume of an average adult human liver when placed directly above it. Note that the 70% value is just a comparison of the robot workspace to the total size of the average liver The inverse kinematics of the robot is used to solve for the joint space positions $x_u, y_u, x_l$ and $y_l$ along with the required needle insertion depth, l, given the desired needle tip position, $T_{desired}=(T_x, T_y, T_z)$, and the needle entry point, $P_{entry}=$ ($P_x$, $P_y$, $P_z$), within the global coordinate frame. The needle vector axis can be defined by $$N = T_{desired} - P_{entry} \quad (5)$$

Using N=($N_x$, $N_y$, $N_z$), we can then solve for the positions of the center of the carriages needed to generate this needle axis vector given by, $$x_u = T_x - \frac{T_z + H}{N_z} N_x \quad (6)$$

$$y_u = T_y - \frac{T_z + H}{N_z} N_y \quad (7)$$

$$x_l = T_x - \frac{T_z}{N_z} N_x \quad (8)$$

$$y_l = T_y - \frac{T_z}{N_z} N_y \quad (9)$$

The insertion depth of the needle, l, is solved for by finding the Euclidean distance between the desired entry point and the location of the desired target, $$l = \|T_{desired} - P_{entry}\| \quad (10)$$

In the clinical workflow the point $P_{entry}$ will be defined by the clinician based on pre-operative imaging. The robot forward and inverse kinematics were implemented in a custom Matlab GUI, whereby $T_{desired}$ and $P_{entry}$ could be input and the coordinates of the upper and lower carriages are solved for to generate the appropriate needle vector axis. These joint space positions in addition to the needle insertion depth are then communicated to the robot over a serial bus to the low-level microcontroller such that the robot can be aligned to the desired location.

Active Motion Compensation Protocol

An active motion compensation protocol is proposed for operating the patient mounted robot. In this protocol, the ablation needle will be automatically deployed towards the liver tumor during the stationary phase of the respiration cycle. The respiratory cycle of the patient will be gated using the GE D690 PET/CT scanner which uses the Varian CT Real-Time Position Management system (Varian Medical Systems, Palo Alto, CA). The Real-Time Position Management system consists of reflectors attached to an external marker placed on the patient's abdomen. The marker motion reflects the breathing pattern of the patient and can be captured by an external camera at a frequency of 30 Hz to obtain a surrogate respiratory signal. The system is able to track the real-time position data even when the respiratory rate changes suddenly. The needle insertion module must complete a full-step insertion when the liver has negligible movement in its static phase and release the needle when the liver undergoes significant movement during its dynamic phase. In order to achieve this protocol, the insertion sequence is divided into four sequential steps: grasp, insert, release, and home. FIG. 7(a) shows the finite element method (FEM) simulation of the FFA motion subject to the pressure input. Retracting the needle can be achieved by alternating the sequence to power the FFA. Note that the operation process must be completed within about 2 s to cover just the static phase as seen in FIG. 7(b). The current prototype of the needle insertion module is capable of inserting the needle at a maximum speed of 1.5 mm/s.

Robotic RFA Clinical Workflow

Figure 9:
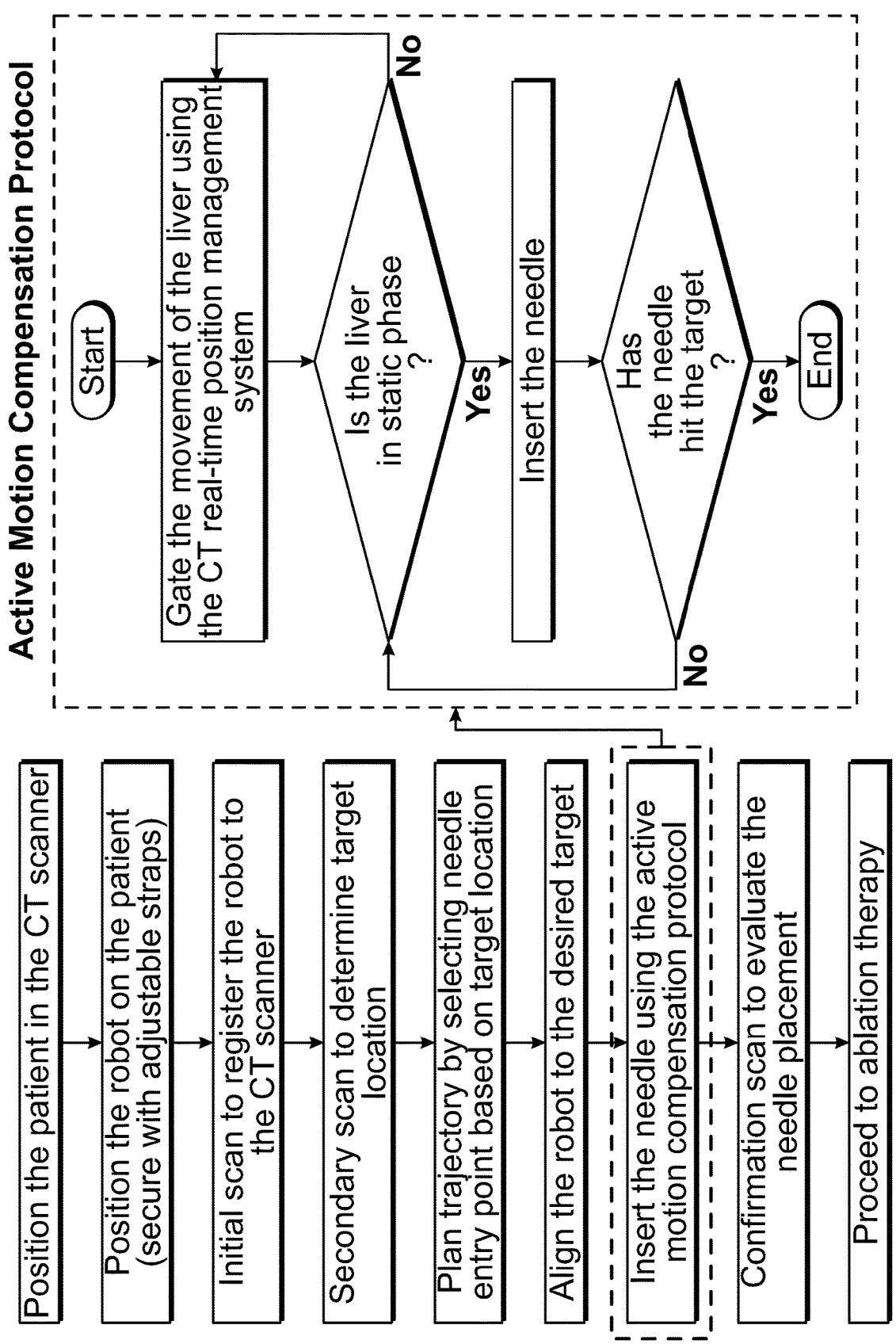
FIG. 9 illustrates a clinical workflow of the robot for an embodiment of the present invention.

In a clinical workflow, the patient will be positioned in a PET/CT scanner and the robot will be fixed to the patient's abdomen using adjustable straps. An initial CT scan will be performed to register the robot to the CT scanner using a point-based registration method. A second CT scan will be used to identify the desired target location, which will be used by the radiologist to determine an appropriate needle entry point. The robot will automatically align the needle insertion module to the desired target and the needle can then be progressed towards the ablation target. During the needle insertion process, the Varian CT Real-Time Position Management system will continuously track the patient's respiratory cycle. According to the proposed motion compensation protocol, the needle is only advanced when the liver has the least amount of motion (static phase, see FIG. 7(b). Once the needle is placed at the target location, a confirmation scan will be conducted to verify the needle location, and ablation therapy will then be performed. The detailed workflow is shown in FIG. 9.

Force Modeling of the Needle Insertion Module

Force modeling of the FFA may be used to estimate the force the FFA is capable of inserting a needle with. The axial force of the linear bellows, $F_A$, is given by, $$F_A = \pi (R + h)^2 \times P \quad (11)$$

where $$x = \frac{(1 - \rho^2)(1 - \rho^4 + 4\rho^2 \ln \rho)}{4(1 - \rho^2 + 2\rho \ln \rho)(1 - \rho^2 - 2\rho \ln \rho)} \quad (12)$$

$$\rho = \frac{R - h}{R + h} \quad (13)$$

The parameter R defines the mean radius of the bellow, and h is half the wave height of a corrugation, as depicted in FIG. 6. In addition to this axial force caused by the linear bellows, the force of friction that the gripper is holding the needle with plays a key role in determining the needle insertion force and should be considered. From a review of the principles from mechanics of materials, the deflection of a thin circular plate with clamped outer edges and a free inner edge is given by $$y_{max} = \frac{Pa^4}{64D} \quad (14)$$

where P is a uniformly distributed pressure over the surface area of the diaphragm, a is the radius of the diaphragm, and D is the flexural rigidity defined in (15) as $$D = \frac{Et^3}{12(1 - v^2)} \quad (15)$$

where E and v are the material properties Young's modulus and Poisson's ratio, respectively, and t is the thickness of the diaphragm. Again, from mechanics of materials, the normal force, $F_N$, acting on the needle due to the deflection of the diaphragms may be derived. The relationship between the normal force and the displacement at the center of the diaphragm is given by, $$y_{max} = \frac{F_N a^2}{16 \pi D} \quad (16)$$

Substituting (14) and (15) into (16) provides the relationship between the input internal pressure of the diaphragm chamber and the normal force generated between the diaphragms and the needle. A scaling factor of 2 is included since the normal force is being applied to both sides of the needle. This relationship is given by, $$F_N = \frac{\pi}{2} P a^2 \quad (17)$$

Using this normal force to pressure relationship, it is possible to estimate the force of friction holding the needle in place by multiplying the normal force by the coefficient of friction, 0.35, of the material. For an input pressure of 345 kPa, an estimated 24.6 N of friction force will be used to clamp onto the needle. This force is considered as more than sufficient for percutaneous needle interventions.

Experiments and Results

Several experiments were conducted to characterize the performance of the robot: a) free-space accuracy evaluation of the 4-DoF dual cartesian stages, b) free-space accuracy and repeatability of the needle insertion module, c) force characterization of the needle insertion module, d) static phantom and static ex-vivo porcine liver tissue targeting, e) dynamic phantom targeting, and f) dynamic ex-vivo porcine liver tissue targeting.

Accuracy Analysis of the Dual Cartesian Stages

Figure 10:
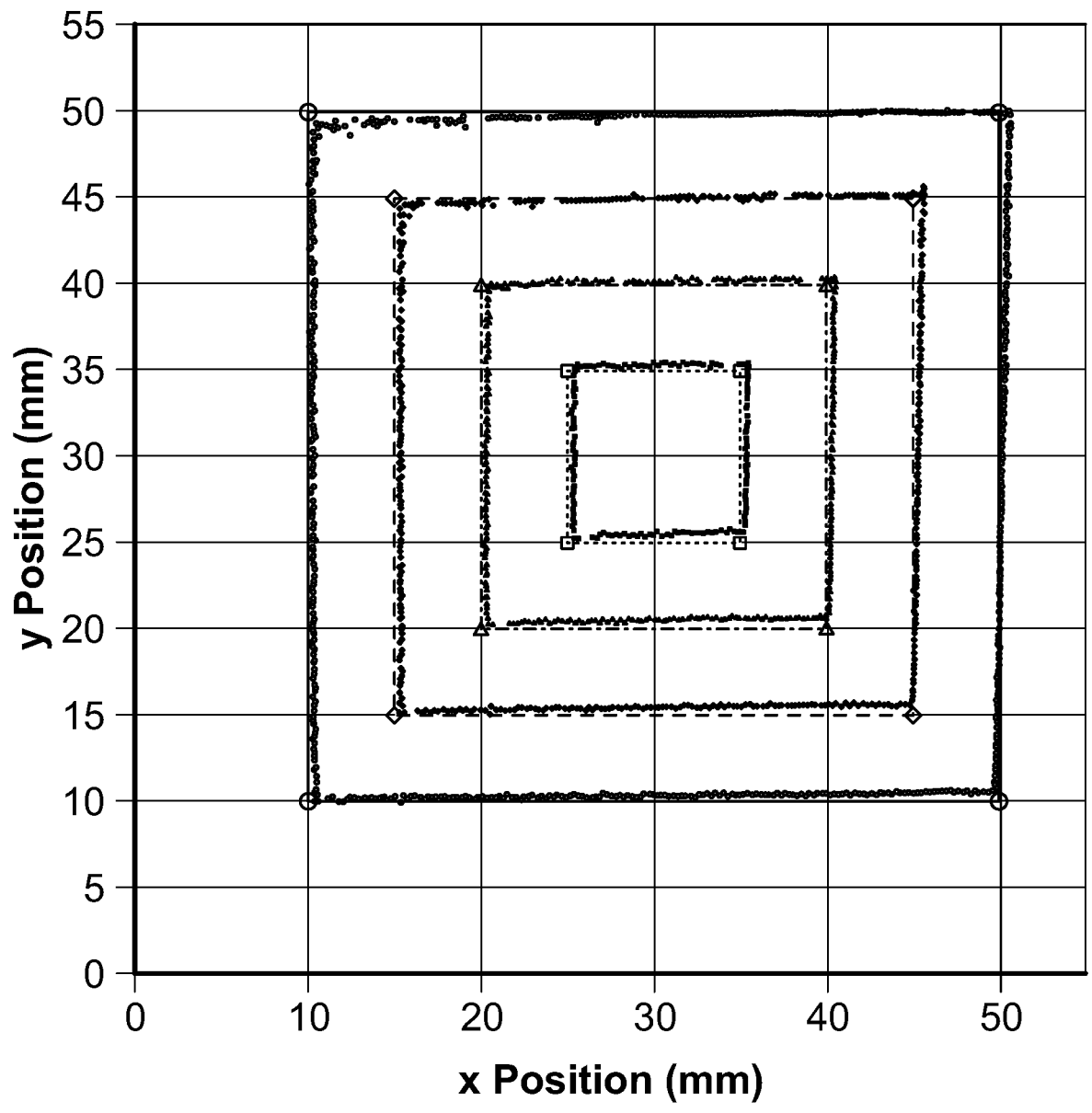
FIG. 10 illustrates a desired path versus the actual tracked path of the Cartesian stages wherein the dashed lines represent the desired path while the dots show the data collected from the EM tracker

To characterize the accuracy of the dual cartesian stages, a free-space analysis was conducted. This was done using the Aurora electromagnetic (EM) tracking system (NDI Medical, Ontario, Canada) with resolution of 0.5 mm. The two carriages were linked together, allowing the central axis between the two carriages to be more easily identified. A 5-DoF EM sensor was used to track the position of the central axis between the carriages. Coordinate registration was done to be able to track the sensor within the robot reference frame using the point-based registration method. The reference frame registration was taken after initially homing both stages of the robot. From there, a desired path was sent to the robot via the Matlab GUI and the real time position was tracked. The desired paths consisted of four squares of length 10 mm, 20 mm, 30 mm, and 40 mm, all created by streamlining the coordinates of the corners of the square to the GUI as seen in FIG. 10. The mean error across three experiments for each desired path was measured at the corners of the squares in both the x- and y-directions. The mean error in the x-direction is 0.18±0.18 mm and the mean error in the y-direction is 0.32±0.23 mm. These free-space experimental results were taken as validation for sufficient accuracy of the dual cartesian system to potentially be used for precise needle placement operations.

Accuracy and Repeatability of Needle Insertion Module

To characterize the accuracy of the needle insertion module, the EM tracker was again used to perform insertion in free-space. An EM sensor was attached to the tip of a needle and a custom 3D printed bracket was used for coordinate registration. The needle used was an 18-gauge needle with diamond shaped tip. Eight insertion depths of 15 mm, 30 mm, 45 mm, 60 mm, 75 mm, 90 mm, 105 mm and 120 mm were sent to the needle insertion module from the GUI for a total of three iterations for each depth. The error was considered to be the difference between the measured insertion depth and the desired depth. The mean error across all 24 experiments was found to be 0.64±0.38 mm (see Table 2 for the error results at each insertion depth). Note that the error does not accumulate as the needle insertion depth is increased due to the step-wise operation of the needle insertion module. This step-wise insertion ensures that the needle insertion error is within one full step-size of the FFA (1.5 mm). The repeatability of the needle insertion module was quantified by evaluating the Coefficient of Variation (CV) [41, 54]. The CV is expressed as a percentage, and the lower the percentage, the better the repeatability is. The results of the needle insertion experiment are presented in Table 2.

TABLE 2

Needle insertion accuracy and repeatability

| Desired Insertion Depth (mm) | Mean Measured Depth (mm) | \|Mean Error\| (mm) | STD of the Measured Depth (mm) | CV % |
|---|---|---|---|---|
| 15 | 15.94 | 0.94 | 0.10 | 0.62 |
| 30 | 30.49 | 0.49 | 0.19 | 0.61 |
| 45 | 44.97 | 0.13 | 0.25 | 0.55 |
| 60 | 60.26 | 0.84 | 0.80 | 1.33 |
| 75 | 76.12 | 1.12 | 0.51 | 0.67 |
| 90 | 90.40 | 0.56 | 0.49 | 0.54 |
| 105 | 105.17 | 0.56 | 0.54 | 0.51 |
| 120 | 120.16 | 0.36 | 0.43 | 0.36 |
| Mean | | 0.64 | 0.38 | 0.65 |

Force Characterization of Needle Insertion Module

Figure 11B:
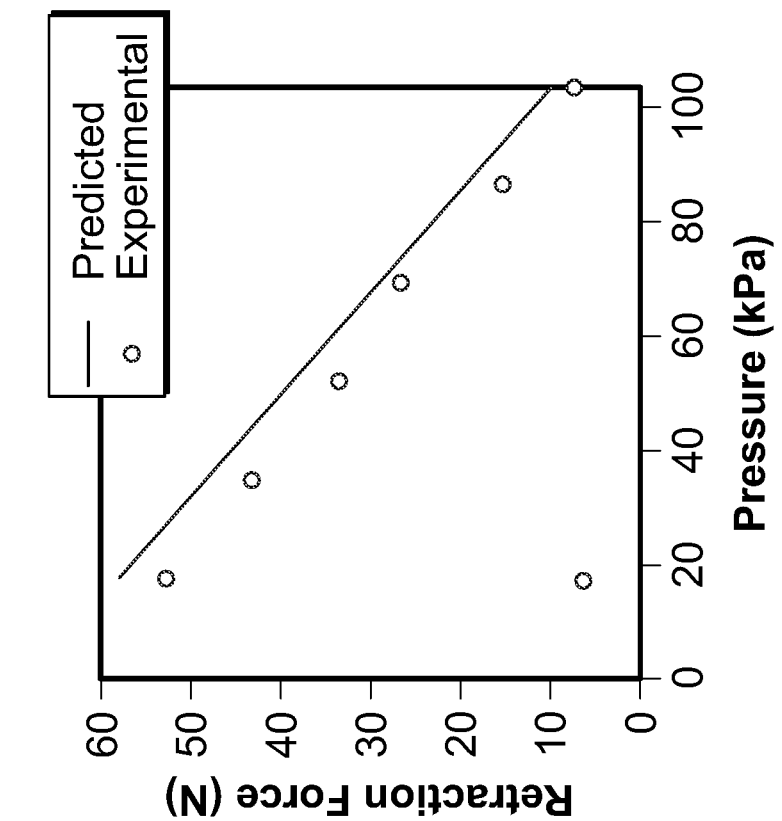
FIGS. 11A, 11B and 11C illustrate the results of the FFA characterization: (a) insertion force characterization results, (b) retraction force characterization results, (c) experimental friction force between the gripper and the needle as the pressure input to the linear bellows is increased compared to the theoretical peak friction force with the pressure input of 345 kPa to the gripper mechanism.
Figure 11A:
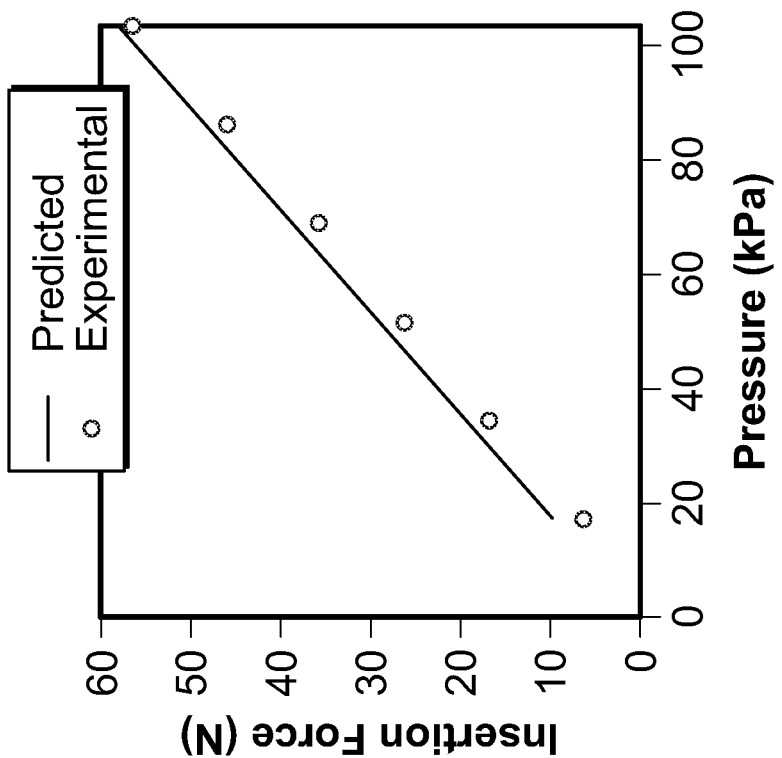

In addition to the insertion testing accuracy in free-space, the forces generated by the FFA were also characterized. The insertion force due to pressurizing the linear bellows was found by placing a force sensor (Vernier Go Direct® Force and Acceleration Sensor) with a flat plate adapter directly against the FFA. The pressure inside the linear bellows was slowly increased from 0 kPa to 110 kPa, corresponding to the maximum force measurable by the force sensor. As the pressure was increased, the insertion force was recorded at intervals of 17.5 kPa (2.5 psi). A custom 3D printed bracket was designed to attach the safety tabs on the FFA to the force sensor. It was configured such that the linear bellows could be pressurized and allow the pulling, retraction force of the bellows to be measured as they were depressurized. As the pressure was decreased, the corresponding retraction force was recorded for the same intervals as previously mentioned. The results of the linear bellows force characterization were compared to the predicted forces calculated using (11)-(13) set forth above as seen in FIGS. 11(a) and (b). A mean error of 2.57±0.6 N was found for the insertion force experiment and a mean error of 4.04±1.39 N was found for the retraction force experiment. These errors can be largely attributed to manufacturing imperfections in the FFA.

Figure 11C:
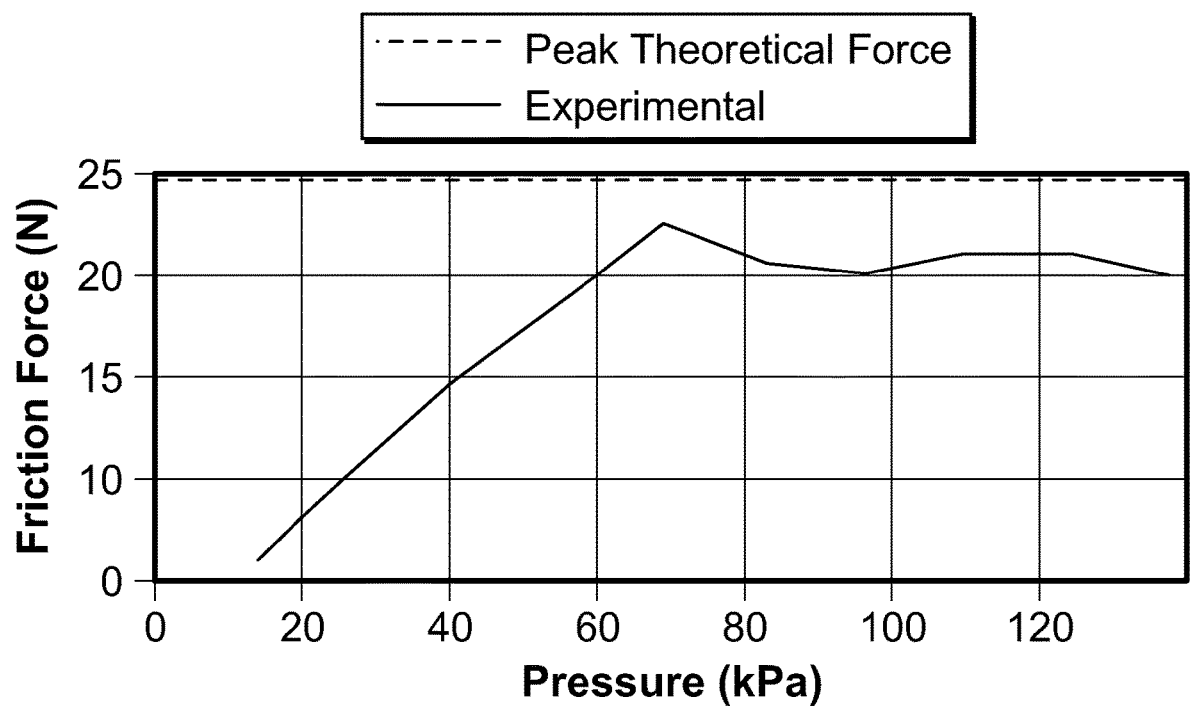

The linear bellows are capable of producing significantly more force than the gripping diaphragms at the same pressure input, therefore it is expected that the needle will slip between the diaphragms at a certain point. To characterize this frictional force, a needle was placed between the grippers at 345 kPa and the force sensor then positioned at the tip of the needle. The pressure inside the linear bellows was then increased and the force at the tip of the needle was monitored. A noticeable peak force was achieved which corresponded to the needle beginning to slip due to the change from static friction to dynamic friction, as seen in FIG. 11(c). Based on the calculations above, a peak force of 24.6 N was expected, while the experimental results indicate a mean peak force of 22.6±0.40 N across three trials. This difference of 8.4% may be as a result of manufacturing imperfections and environmental conditions affecting the coefficient of friction between the two materials. The linear bellows force characterization and the friction force analysis both indicate more than sufficient force is achievable to perform percutaneous liver interventions, where a peak force of about 6 N was recorded for the percutaneous interventions based on previously mentioned research.

Robot Targeting Test: Static Phantom and Ex-Vivo Porcine Liver Trial

A 5% by volume agar gelatin phantom was created to mimic soft liver tissue. The experiment was conducted by selecting 24 arbitrary points, grouped into four groups of 6 points, within the robot's workspace and using their xy-location as the desired target. For the first group of six points, the desired insertion depth was increased from 15 to 90 mm in 15 mm increments across the points and the needle orientation was set to 0°. This was then repeated for the remaining three groups however the needle orientation about the x-axis was increased in 5° increments across the groups. Using these values as the desired input to the robot GUI, the needle was placed and automatically deployed to the phantom via the needle insertion module. The final location of the needle was recorded by the EM tracker. Each targeting experiment was conducted three times and the mean values were used in quantifying the accuracy of the robot. The positional error was defined to be the Euclidean distance between the desired target and the measured location. Additionally, the orientational error is defined by the difference between the desired input angle and the measured angle. The results for the static phantom experiment show that there is a mean positional error of 1.14±0.30 mm and an orientational error of 0.99°±0.36°.

Figure 12:
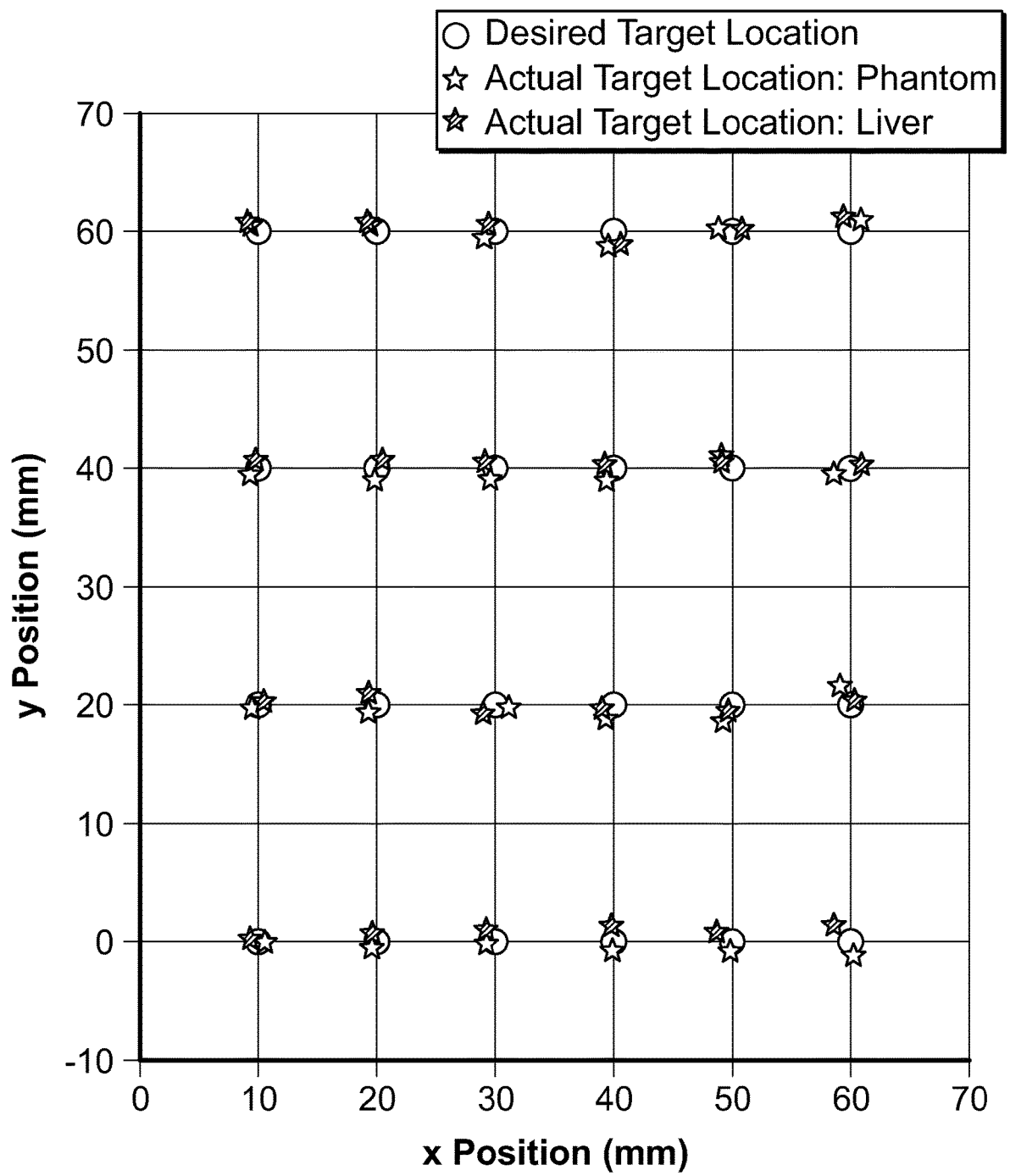
FIG. 12 is a top view of the static targeting experiments. The circles represent the desired target location, the stars show the measured needle position in the static phantom, and the solid stars show the measured needle position in the static ex-vivo porcine liver.
Figure 13:
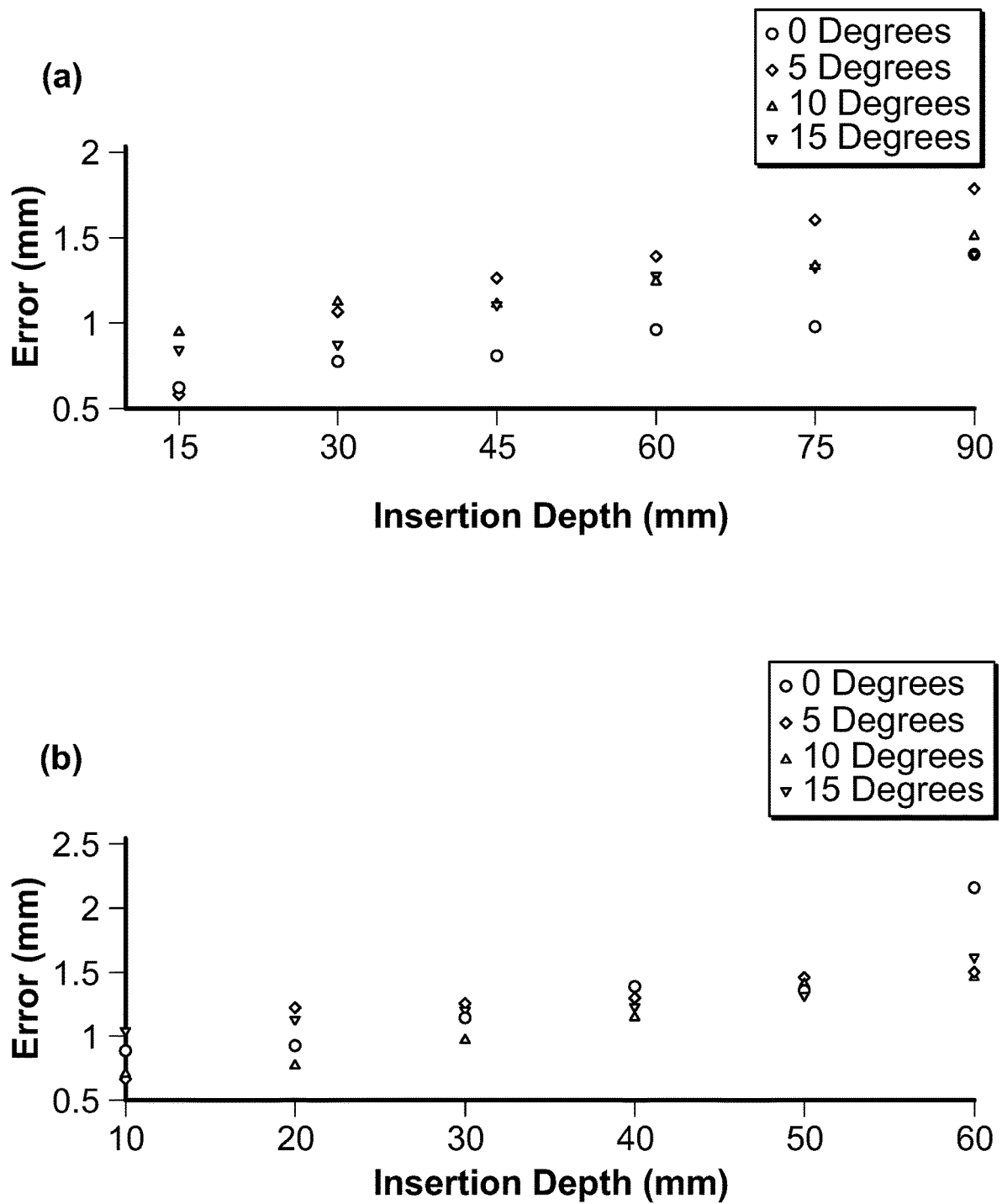
FIG. 13 illustrates (a) Static phantom needle targeting error vs. insertion depth (b) Static ex-vivo porcine liver needle targeting error vs. insertion depth. In both tests, the needle insertion angle was increased from 0° to 15° in increments of 5°.

The same points and grouping scheme was used to repeat the experiment in a static ex-vivo porcine liver except the insertion depth increased from 10 to 60 mm in increments of 10 mm, where 60 mm was the maximum thickness of the porcine liver sample used. Porcine liver has often been used to mimic an environment for testing needle insertion devices in place of human tissue. The porcine liver was acquired fresh from a local meat supplier, and prior to testing the liver was allowed to come to room temperature. The results show that there is a mean positional error of 1.22±0.31 mm and an orientational error of 1.16°±0.44°. A top view of the static targeting experiments can be seen in FIG. 12. There is a slight increase in positional targeting error of the needle with respect to the insertion depth in both the static phantom and ex-vivo liver trials. This can be seen in FIG. 13 where there is a general increasing trend in the positional error as the insertion depth is increased. The targeting error, however, does not show any significant statistical relation to the increasing inclination of the needle.

Robot Targeting: Dynamic Phantom Trial

To validate the robot's targeting performance under the dynamic conditions of the liver, a dynamic motion platform was developed to create a relative displacement between the robot and the phantom. The motion platform consists of two stepper motor driven linear rails fixed to one another perpendicularly in the horizontal plane. A two-dimensional dynamic phantom was chosen rather than considering three-dimensional motion for two primary reasons. It has been found that liver motion in the inferior-superior (I-S) and left-right (L-R) is dominant in comparison to the motion generated in the posterior-anterior (P-A) direction (~1.2 mm).

A two-dimensional dynamic motion platform also greatly simplified the robotic motion platform, especially during the prototype characterization period. Between every two steps of the needle insertion process, the motion platform moves the phantom 10 mm in the x-direction and 5 mm in the y-direction to simulate the respiratory induced motion of the liver in the I-S direction and L-R direction, respectively. While the phantom is in motion, the needle insertion module releases the needle to allow it to move with the phantom freely. Once the platform has returned to its original position, the needle insertion module takes another two full insertion steps and the process is repeated until the needle has reached its final target.

The stepwise "move-pause" insertion protocol is inspired by the manual insertion procedure, where the clinician typically inserts the needle when the liver has the least motion and releases the needle when respiration motion is significant. Twenty-four targets were selected by arbitrarily inserting the 6-DoF EM tracking probe (NDI Medical, Ontario, Canada) into the phantom. The location of the target, the tip of the EM tracking probe, was then converted into the robot frame and used as an input for the GUI. Similarly to the static phantom trial, the 24 points were grouped into 4 groups of 6 and the desired insertion depth of the needle was user controlled from 15 to 90 mm in 15 mm increments while the needle orientation across each group was increased from 0° to 15° in increments of 5°. Three insertion trials were conducted for each target and the error for these dynamic targeting experiments is defined to be the same as in the static experiments. The results of the dynamic targeting experiments in phantom indicate a mean positional error of 1.69±0.66 mm and a mean orientational error of 1.66±0.50°.

Figure 14:
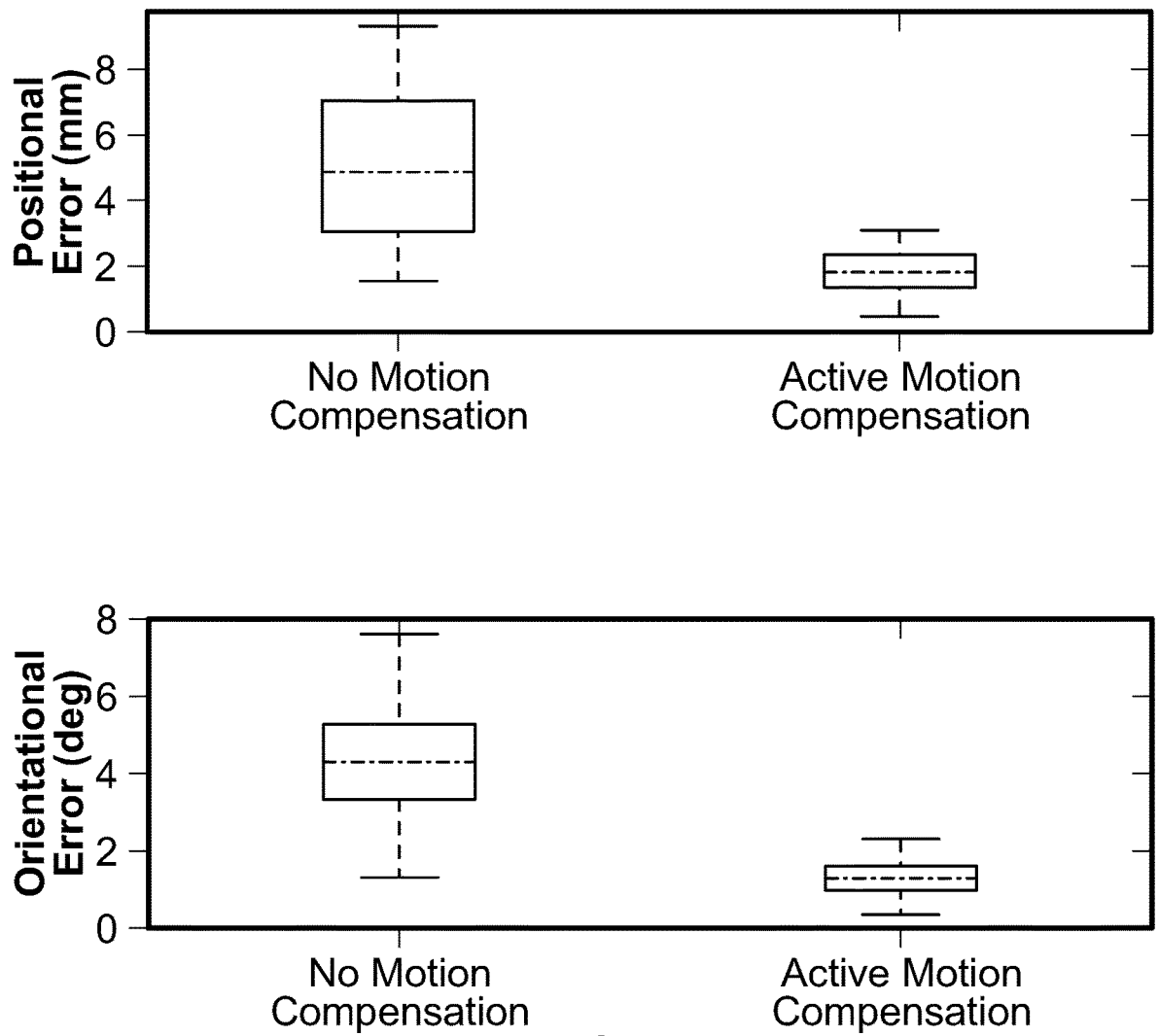
FIG. 14 is a comparison of dynamic phantom targeting experiments with and without active motion compensation.

The dynamic targeting experiments were repeated, however, this time no motion compensation was considered. The synchronicity between the needle insertion module and the motion platform was disabled so that there was no consideration of the location of the moving target with respect to the insertion of the needle. The needle was inserted with constant speed until it reached its final target, the motion platform was simultaneously stopped, and the final needle position was recorded. The results of this dynamic targeting experiment with no motion compensation indicates a mean positional error of 5.02±2.35 mm and a mean orientational error of 4.54±1.40°. A comparison between the dynamic phantom targeting experiments with active motion compensation and without motion compensation is shown in FIG. 14.

Robot Targeting: Dynamic Ex-Vivo Porcine Liver Trial

Figure 15:
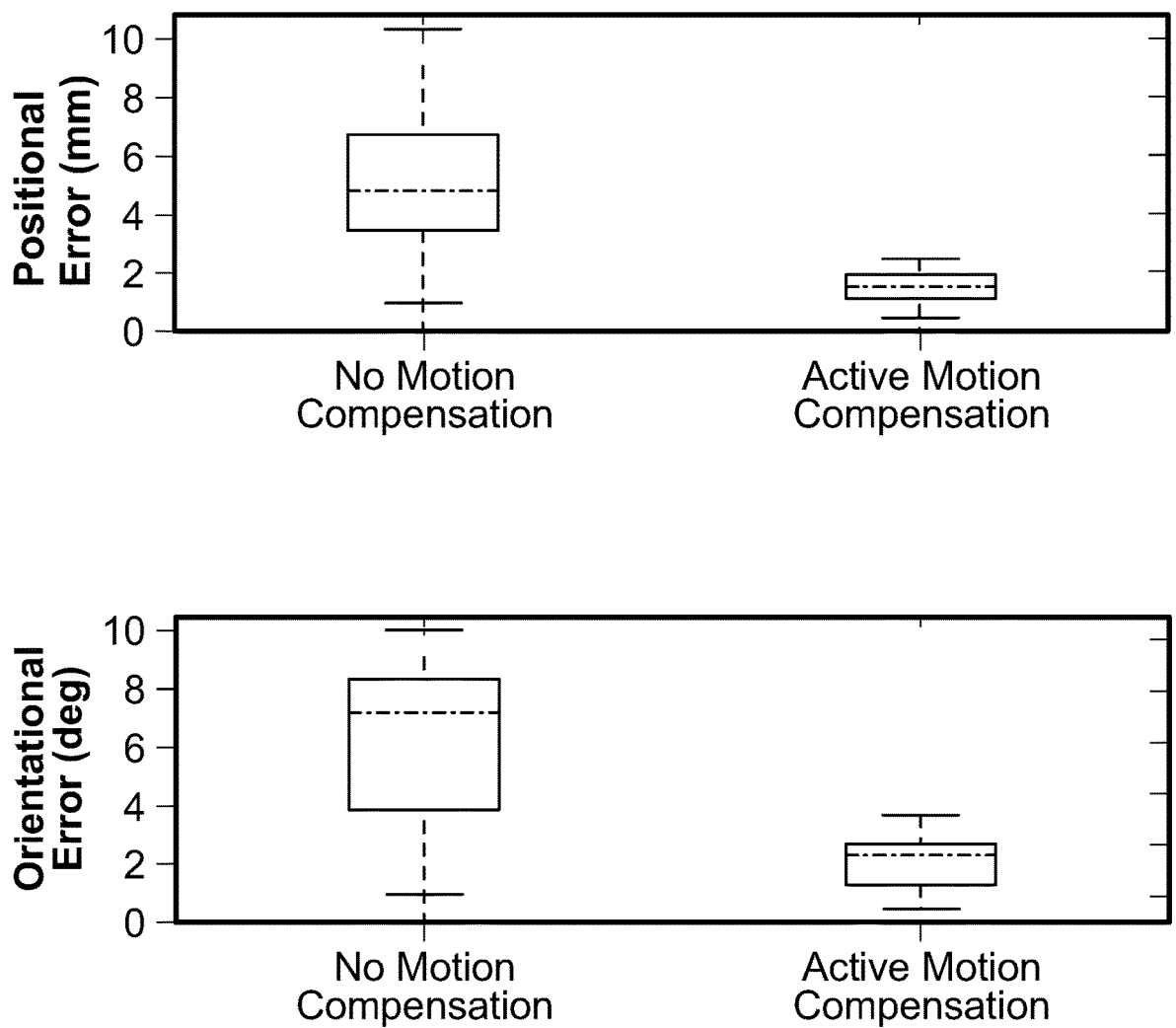
FIG. 15 is a comparison of ex-vivo porcine liver dynamic targeting experiments with and without active motion compensation
Figure 16A:
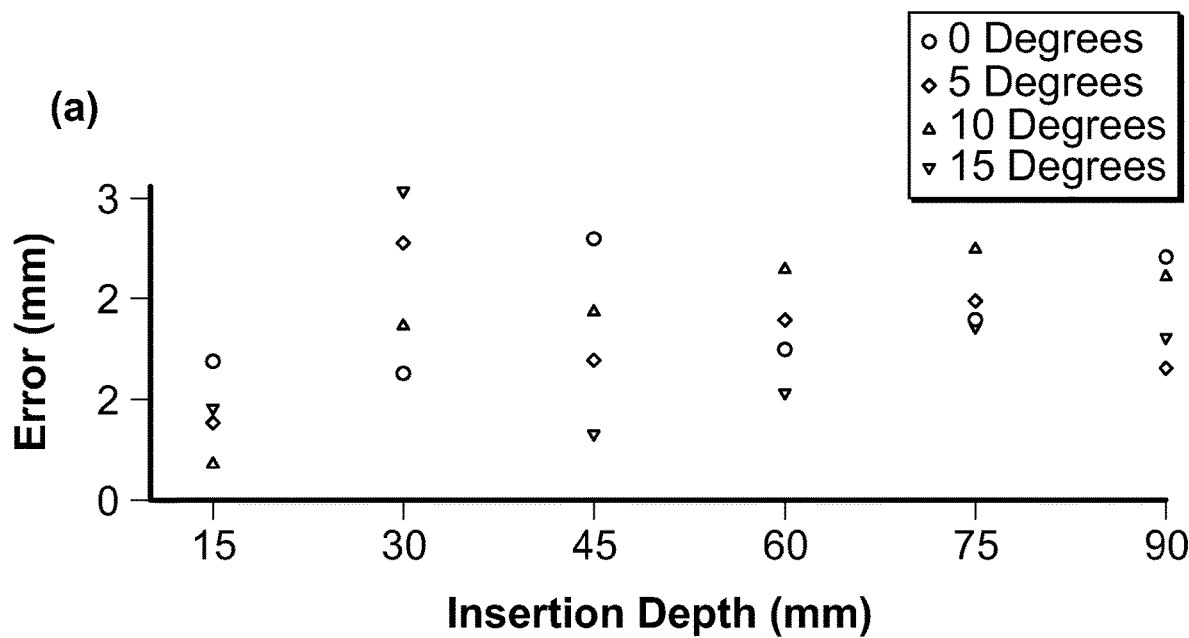
FIGS. 16A and 16B illustrate (a) Dynamic phantom needle targeting error vs. insertion depth (b) Dynamic ex-vivo porcine liver needle targeting error vs. insertion depth. In both experiments, the needle insertion angle was increased from 0° to 15° in increments of 5°.
Figure 16B:
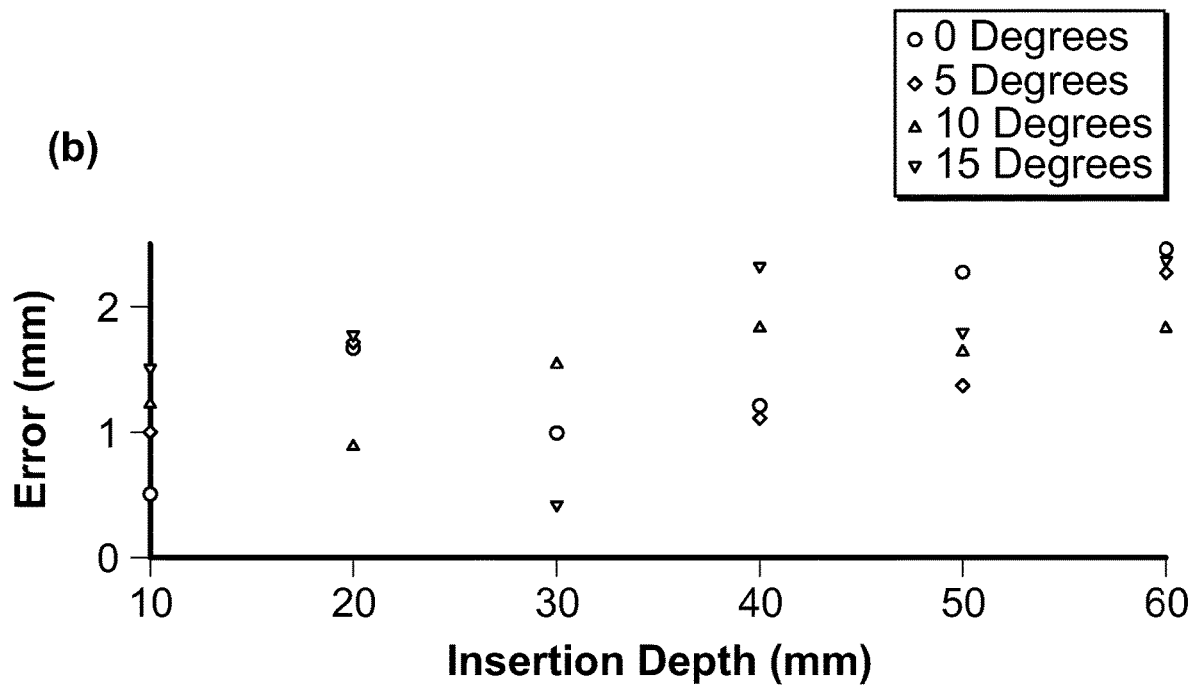

To simulate targeting in biological tissue, an ex-vivo porcine liver sample was used in place of the agar phantom. The same workflow used in the dynamic phantom targeting experiments was employed here for a total of 24 targets. With the motion compensation protocol implemented, the results indicate a mean positional error of 1.54±0.55 mm and a mean orientational error of 1.68±0.47°. The experiments were repeated without the motion compensation protocol implemented and the results show a mean positional error of 5.07±2.44 mm and a mean orientational error of 4.06±1.45°. A comparison of these results is presented in FIG. 15. Similar to the static experiments, a slight increase in positional targeting error was observed in both the phantom and ex-vivo liver trials, more noticeably in the ex-vivo liver as seen in FIG. 16. Again, no noticeable statistical correlation could be made between targeting error and increasing inclination of the needle.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above-described embodiments, methods, and examples, but by all embodiments and methods within the scope and spirit of the disclosure.

What is claimed is:

1. A robotic platform system that enables accurate needle deployment in the dynamic environment of the liver comprising: (1) a lower stage with a motorized cartesian carriage, (2) an upper stage with a motorized cartesian carriage, and (3) a needle insertion module that connects both stages together; and (4) wherein said needle insertion module includes a flexible fluidic actuator adapted to insert and retract a needle.

2. The system of claim 1 wherein the upper and lower stages have carriages that can move in both the x and y directions.

3. The system of claim 2 wherein the carriages both have spherical bearings set into them that support said needle insertion module and by changing the relative location between the bearings, the orientation of the needle insertion module can be controlled about the x and y axes.

4. The system of claim 3 wherein said flexible fluidic actuator includes one or more inflatable bellows adapted to move a needle linearly when said one or more bellows are inflated.

5. The system of claim 4 wherein said flexible fluidic actuator includes one or more diaphragms that hold a needle stationary within said robot when inflated.

6. The system of claim 5 wherein, when a needle is to be inserted further into a patient, said one or more diaphragms are inflated prior to said inflation of said one or more bellows, and wherein said system includes a gap between said needle and said one or more diaphragms and one or more bellows when said one or more diaphragms and one or more bellows are deflated.

7. The system of claim 6 wherein said upper and lower stages are identical.

8. The system of claim 7 further including, a linear optical encoder and a linear transmissive strip, said optical encoder and linear transmissive strip adapted to provide the relative displacement of said flexible fluidic actuator.

9. The system of claim 8 wherein said gap eliminates contact between said needle and said bellows and said one or more diaphragms when said one or more bellows and said one or more diaphragms are deflated.

10. The system of claim 8 wherein said needle does not contact said one or more bellows and said one or more diaphragms when said one or more bellows and said one or more diaphragms are deflated.

11. A method for accurate needle deployment in the dynamic environment of the liver comprising the steps of:
providing a robotic platform having (1) a lower stage with a motorized cartesian carriage, (2) an upper stage, and (3) a needle insertion module that connects both stages together;
said upper and lower stages have carriages that can move in both the x and y directions;
said insertion module includes a flexible fluidic actuator adapted to insert and retract a needle;
said flexible fluidic actuator includes one or more inflatable bellows adapted to move a needle linearly when said bellows are inflated and one or more diaphragms that hold a needle stationary within said robot when inflated;
when a needle is to be inserted during a static phase of a liver, said one or more diaphragms are inflated to grip the needle, then said one or more bellows are inflated to insert the needle; and
prior to a liver transitioning out of a static phase, said one or more inflatable diaphragms are deflated and then said one or more bellows are deflated.

12. The method of claim 11 wherein said needle is allowed to move freely without interference within said fluid actuator when said needle is not being inserted.

13. The method of claim 11 further including a linear optical encoder and a linear transmissive strip, said optical encoder and linear transmissive strip adapted to provide the relative displacement of said flexible fluidic actuator.

14. The method of claim 11 further including a gap between said needle and said one or more diaphragms and said one or more bellows when said one or more diaphragms and said one or more bellows are deflated.

15. The method of claim 14 wherein said gap eliminates contact between said needle and said one or more bellows and said one or more diaphragms when said one or more bellows and said one or more diaphragms are deflated.

16. The method of claim 11 wherein said needle does not contact said one or more bellows and said one or more diaphragms when said one or more bellows and said one or more diaphragms are deflated.

17. The method of claim 11 wherein said needle is inserted for around 2 seconds.

18. The method of claim 11 wherein said upper and lower stages are identical.

* * * * *